(12) United States Patent
Chen

(10) Patent No.: US 10,105,705 B2
(45) Date of Patent: Oct. 23, 2018

(54) DEVICE AND METHOD FOR CHEMICAL, BIOCHEMICAL, BIOLOGICAL AND PHYSICAL ANALYSIS, RE-ACTION, ASSAY AND MORE

(75) Inventor: Guo Jun Chen, Moehlin (CH)

(73) Assignee: NCL NEW CONCEPT LAB GMBH (CH)

( * ) Notice: Subject to any disclaimer, the term of this patent is extended or adjusted under 35 U.S.C. 154(b) by 1343 days.

(21) Appl. No.: 12/295,706

(22) PCT Filed: May 2, 2007

(86) PCT No.: PCT/IB2007/001132
§ 371 (c)(1),
(2), (4) Date: Oct. 9, 2008

(87) PCT Pub. No.: WO2007/125407
PCT Pub. Date: Nov. 8, 2007

(65) Prior Publication Data
US 2009/0181463 A1 Jul. 16, 2009

Related U.S. Application Data

(60) Provisional application No. 60/797,025, filed on May 3, 2006.

(51) Int. Cl.
*B01L 3/00* (2006.01)
*G01N 21/03* (2006.01)
(Continued)

(52) U.S. Cl.
CPC ...... *B01L 3/50857* (2013.01); *G01N 21/0303* (2013.01); *G01N 21/645* (2013.01);
(Continued)

(58) Field of Classification Search
CPC ........... B01L 2300/0829; B01L 3/5027; B01L 3/5082; B01L 2200/10; B01L 2300/0838;
(Continued)

(56) References Cited

U.S. PATENT DOCUMENTS 3,200,650 A * 8/1965 Morrill, Jr. ............. B01L 3/021
422/922
3,807,235 A * 4/1974 Lefkovits ................ B01L 3/021
422/922
(Continued)

FOREIGN PATENT DOCUMENTS

EP 0082263 A1 6/1983
WO 01/85342 A1 11/2001

OTHER PUBLICATIONS

Millar "Tips and Tricks for the Lab: How to Make a Capillary TLC Spotter", ChemistryViews, Jul. 2012, p. 1.*

*Primary Examiner* — Jill A Warden
*Assistant Examiner* — Dwayne K Handy
(74) *Attorney, Agent, or Firm* — Agris & von Natzmer LLP; Joyce von Natzmer

(57) ABSTRACT

The invention is directed to a device and a method for carrying out experiments of chemical, biochemical, biological and physical analysis, reaction and assay employing a reaction unit, in a preferred embodiment comprising: a capillarity reaction chamber, non-capillarity zone and bottom structure, which can use capillary action to quantitatively take up by itself and hold liquid in the reaction chamber. A multi-unit plate, which contains a number of reaction units on a plate frame, can be used for parallel experiments in conjunction with reservoir plate, waster pad, and liquid transfer guider.

13 Claims, 10 Drawing Sheets

(51) Int. Cl.
*G01N 21/64* (2006.01)
*B01L 3/02* (2006.01)

(52) U.S. Cl.
CPC .......... *B01L 3/0241* (2013.01); *B01L 3/0275* (2013.01); *B01L 3/5025* (2013.01); *B01L 2200/0605* (2013.01); *B01L 2300/0627* (2013.01); *B01L 2300/0829* (2013.01); *B01L 2400/0406* (2013.01); *G01N 2021/0346* (2013.01); *G01N 2021/6482* (2013.01); *Y10T 436/25* (2015.01); *Y10T 436/2575* (2015.01)

(58) Field of Classification Search
CPC ..... B01L 2300/0864; B01L 2300/0832; B01L 2300/0848; B01L 2400/0406; B01L 3/0275; B01L 3/502; B01L 3/5025; B01L 3/50857
See application file for complete search history.

(56) References Cited

U.S. PATENT DOCUMENTS

| | | | | |
|---|---|---|---|---|
| 3,952,599 | A * | 4/1976 | Ayres | 73/864.02 |
| 6,372,185 | B1 * | 4/2002 | Shumate et al. | 422/100 |
| 6,551,557 | B1 * | 4/2003 | Rose | B01J 19/0046 |
| | | | | 422/502 |
| 7,305,896 | B2 * | 12/2007 | Howell et al. | 73/864.02 |
| 2003/0124599 | A1 | 7/2003 | Chen et al. | |
| 2005/0069949 | A1 | 3/2005 | Humenik et al. | |
| 2005/0112776 | A1 * | 5/2005 | Clark | B01L 3/0275 |
| | | | | 436/180 |
| 2005/0181519 | A1 * | 8/2005 | Karg et al. | 436/180 |

\* cited by examiner

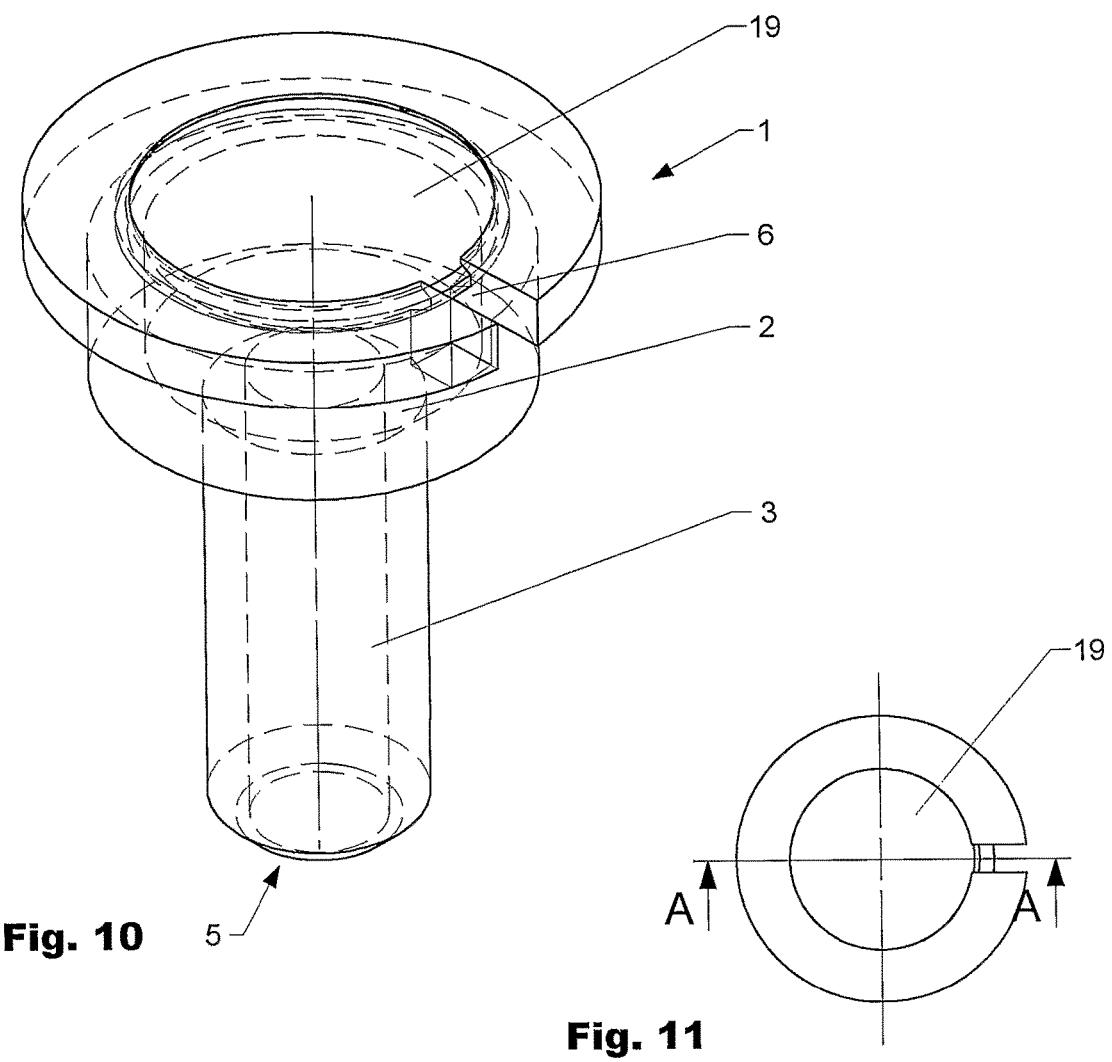
Fig. 10
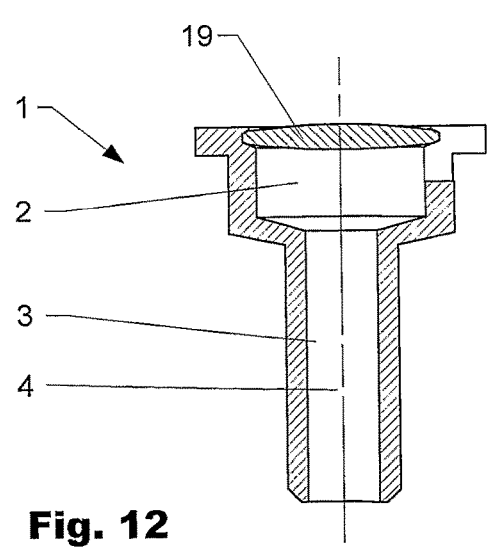
Fig. 11
Fig. 12 a)

b)

DEVICE AND METHOD FOR CHEMICAL, BIOCHEMICAL, BIOLOGICAL AND PHYSICAL ANALYSIS, RE-ACTION, ASSAY AND MORE

This is the U.S. national stage of International application PCT/IB2007/001132, filed May 2, 2007 designating the United States, which claims the benefit of U.S. provisional application 60/797,025, filed May 3, 2006.

FIELD OF THE INVENTION

The present invention relates to a device and a method for carrying out experiments of chemical, biochemical, biological and physical analysis, reaction and assay. The present invention also relates to a device and a method for parallel processing and analyzing of chemical, biochemical or biological sample. The present invention further relates to a device and a method used for sampling, transfer, distribution, storage, dilution and extraction of chemical, biochemical or biological sample.

BACKGROUND OF THE INVENTION

Miniaturization is a development tendency of modern analytical science and technology because for biotech and pharmaceutical industry it means not only to use less limited samples, precious chemical compounds and expensive reagents, but also to increase sensitivity and to reduce incubation time for some types of assay relaying on the ratio of volume to surface area of the reaction well or tube, such as Enzyme Linked Immunosorbent Assay (ELISA). But a miniaturized analytical system that uses a micro-well plate will arise difficulties and problems for quantitative liquid transfer into or from a tiny well even with automations. The existing liquid handling techniques of pipetting, piezoelectric droplet dispensing, split pin dispensing, and microspritzing can easily cause contamination of neighboring wells and loss of sample volume resulting from substantial splashing and entrapment of air bubbles.

High throughput screening assays and techniques of various types are largely used for the discovery and development of new therapeutic agents by companies from small biotech to international pharmaceutical giants. These assays are often carried out at a reduced volume in multi-well plates in order to reduce the cost and save valuable samples. Currently the 96-, 384-, or 1536-well format multi-well plates are principally used in high throughput screening assays. Because a number of pipetting steps are involved in the assay procedure, manually performing high throughput assay in the 96-well format is already very tedious and can easily introduce manmade pipetting mistakes. Although automated assay systems may enable to increase the high-throughput screening capacity of a wide variety of biochemical and molecular biology tests such as enzymatic activity, receptor binding, macromolecular interactions, protein expression, and protein folding and assembly, but the extremely expensive robotic systems may not be affordable for small biotech companies and is not worthwhile to buy even for big pharmaceutical companies to carry out only limited screens. So far, there is no dramatic progress for miniaturized assays needing separation steps like ELISA.

Multiplexed detection technique is also a trend of the modern analytic techniques, which allows simultaneously detecting various analytes from one single sample. This technique is particular useful for diagnosis, clinical study and pathway identification. Although protein micro-array technology can meet the multiplexed detection requirement, some technical difficulties still exist. For example, it is not designed for high throughput and manual performance. The reaction conditions for all analytes are the same. Furthermore, the extremely high cost for the automation and the protein chip will be an insurmountable barrier for it being widely used.

On the eve of worldwide outbreak of bird flu, it urgently needs a cost-effective, easy-to-use, robust, rapid, and high throughput micro-assay system capably to test an enormous amount of samples by assays like ELISA in order to monitor, prevent and control the epidemic situation. Hospital, biotech and pharmaceutical industry, academic institute and university, agriculture, food and beverage industry also welcome such a technology.

OBJECTS OF THE INVENTION

In view of the disadvantages described above, it is an object of the present invention to provide a device and a method for chemical, biochemical, biological and physical experiments of analysis, reaction and assay, in a reduced volume.

It is another object of the present invention to provide devices and methods for the ease of liquid transfer in or from the reaction chambers quantitatively.

It is still another object of the present invention to provide devices and methods for the ease of parallel, quantitative liquid transfer in or out of the reaction chambers.

It is still another object of the present invention to provide devices and methods for the ease of quantitative sampling of chemical, biochemical or biological samples.

It is still another object of the present invention to provide devices and methods for the ease of quantitative liquid transfer of chemical, biochemical or biological samples.

It is still another object of the present invention to provide devices and methods for quantitative chemical, biochemical or biological sample storage.

It is still another object of the present invention to provide devices and methods for the ease of chemical, biochemical or biological sample dilution.

It is still another object of the present invention to provide devices and methods for the ease of chemical, biochemical or biological sample extraction.

It is still another object of the present invention to provide devices and methods for performing multiplexed detection of chemical, biochemical or biological samples.

It is still another object of the present invention to provide devices and methods for manually high-throughput processing and analyzing of chemical, biochemical or biological samples with the same or similar accuracy and speed as automation.

SUMMARY OF THE INVENTION

The difficulties in quantitatively transferring small amount of liquid into and/or out of a tiny well for an experiment or an application is the bottleneck of further miniaturizing analysis, reaction and assay system as well as of further increasing capacity of high throughput. In order to solve this problem, the present invention provides devices and methods to ease liquid transfer for a low volume experiment of chemical, biochemical, biological and physical analysis, reaction and assay. The present invention also includes devices and methods by which many chemical, biochemical, biological, or physical experiments can be implemented in a parallel processing and analyzing manner.

The present invention further includes devices and methods for quantitative sampling, transfer, distribution, storage, dilution and extraction of chemical, biochemical or biological samples.

In general, according to the present invention an experiment is performed in a device called reaction unit. In an embodiment the reaction unit comprises a capillarity reaction chamber being able to take up liquid quantitatively by itself and/or to hold quantitative amount of liquid inside based on capillary action. The reaction chamber is in general formed by a reaction unit body and normally has open structure to allow liquid and air to pass through during liquid transfer.

When looking at a cross-section of a reaction unit, it is possible to distinguish a closed reaction chamber and an opened reaction chamber. The closed reaction chamber has no additional open structure on its body except of the open structure for liquid and air to pass through at both ends whereas the opened reaction chamber has at least one additional open structure on its body. In some embodiments, the reaction chamber is open to a non-capillarity zone of the reaction unit, which does not permit liquid to remain inside but has open structure at least for air to pass through. In still some embodiments, a bottom structure of the reaction unit may attach to the reaction chamber to serve as a channel at least for liquid passing through.

Various configurations of the reaction chamber and/or the non-capillarity zone and/or the bottom structure in the reaction unit are suitable for use with the present invention. They may run length-wise along their axes at any angles from parallel to perpendicular with a major axis of the reaction unit. In a preferable embodiment, all of them run length-wise along the major axis of the reaction unit.

In an embodiment, a reaction unit has a configuration to allow a light beam to pass through the inner space of the reaction unit without objects but the sample.

Depending on the field of application, the cross-section of the reaction chamber, the non-capillarity zone or the bottom structure may have a cross-section, which is circular, triangular, square, rectangular, or a combination therefore. In an embodiment, a reaction chamber has at least partially a rough surface to increase surface area and/or liquid adhesion in order to form a liquid thin layer on the surface when liquid is emptied from the reaction chamber.

If appropriate the reaction chamber is shaped/has a geometry to increase light receiving area, e.g. by a cone shape reaction chamber. The surface geometry may be shaped such that optical signals produced from the analytes inside the reaction chamber are directed towards an open structure. It is also possible to that whole or part of a reaction unit contains a layer of material to which reduces the optical signal loss and/or reduce the optical contamination and/or produce evanescence and/or to resist chemical interaction and other objectives.

In some embodiments, non-capillarity zone or bottom structure or both can also serve as a light guiding device to define the light path in the reaction unit.

In an embodiment, geometric forms of a non-capillarity zone can direct coming light to the reaction chamber or optical signal from the reaction chamber to a detector.

In an embodiment, a build-in lens maybe installed on the top of the non-capillarity zone with a focus onto the reaction chamber.

In some embodiments, a reaction unit may have more than one capillarity reaction chamber.

In an embodiment, whole or part of a reaction unit can be made of any kind solid material that may or may not allow particular molecules, for example protein, nucleic acid, and lipid, or biological agents, like virus, micro-organisms, and cell, or small manmade particles to bind onto reaction chamber surface. Alternative, at least part of reaction chamber surface is physically or chemically treated to be able or unable to absorb particular molecules or biological agents or small manmade particles.

In an embodiment, a reaction chamber contains porous material inside for example a gel, a bead, sintered glass, or particulate matter for particular molecules or biological agents.

In an embodiment, the reaction chamber comprises at least one electrode in any forms.

In an embodiment, the reaction chamber comprises at least one build-in optical fiber.

In an embodiment, the reaction chamber comprises at least one build-in micro ultrasound device.

In an embodiment, the reaction chamber comprises at least one build-in sensor of any kind.

A method for handling of liquids with a reaction unit according to the invention in an experiment or an application comprises, but is not limited to, the following process steps:

In an embodiment, quantitative full loading is carried out by contacting of the bottom open structure of the reaction unit with liquid to draw the liquid into the reaction chamber.

In an embodiment, a mechanical vibration process is applied during the quantitative full loading.

In an embodiment, quantitative partial loading is also possible by contacting of the open structure with a desired amount of liquid on a non-wetting surface, which is not enough to fully fill up the reaction chamber.

In an embodiment, several quantitative loadings are also possible by repeating the above quantitative partial loading procedure when total amount of liquid does not exceed the volume of the reaction chamber.

Alternatively, quantitative full or partial loading can be carried out by pipetting desired amount of liquid into the non-capillarity zone or by pipetting directly into the reaction chamber.

In an embodiment, total amount of liquid in the reaction chamber can be emptied by using capillary action in which the open structure of the reaction unit contacts dry or wet material(s) having much stronger capillary action than the reaction chamber for the liquid (e.g. in case of aquatic solution filter paper can be used) to draw the liquid out, by using air pressure to force the liquid to the non-capillarity zone and sucking off using a device for example pipette, by using vacuum, by using centrifugation or by using air flow or pressure to directly drive the liquid out.

In an embodiment, quantitative partial amount of liquid can be removed from the reaction unit by forcing the liquid to the non-capillarity zone and sucking off desired amount from the non-capillarity zone or directly suck off from the reaction chamber by a liquid transfer device for example pipette.

In another embodiment, quantitative partial amount of liquid can be removed from the reaction unit by transferring liquid onto a wettable surface through spotting.

In an embodiment, to replace first liquid totally and quantitatively one can add second liquid to the non-capillarity zone with one or several volume of the reaction chamber when the bottom opening of the reaction unit contacts the surface of the second liquid. The second liquid will push the first liquid out off reaction chamber to replace the old one.

In an embodiment, to replace first liquid partially and quantitatively one can add second liquid in a desired volume to the non-capillarity zone when the bottom opening of the reaction unit contacts the surface of the first liquid. The second liquid will push the first liquid out off reaction chamber in the same amount.

In an embodiment, mixing of liquid in the reaction chamber one can apply an oscillation of air pressure through the open structure of the reaction unit. The oscillation of air pressure shall force the liquid vibration in the reaction unit. For example the liquid first moves towards the non-capillarity zone and then moves back to its original position.

In another embodiment, a certain frequency of mechanical or sound wave can be used to mix the liquid.

In still another embodiment, a reaction unit containing build-in electrodes or build-in micro ultrasound device can be used to force molecules moving in the reaction chamber in order to mix the liquid.

A. Multi-Unit Plate

According to the invention, a device for carrying out experiments in parallel, the multi-unit plate or strip comprises a plurality of reaction units as described which are incorporated or attached to a plate body. In general the reaction units are at least partially protruding from the plate body. Preferably, the major axis of each reaction unit is perpendicular to the planner of the plate body. The multi-unit plate is adapted, in a format of e.g. 2, . . . , 96, 384, 1536 or more, for use in conjunction with a reservoir plate for example a conventional 96-well format plate and waste pad for liquid transfer. In an embodiment, the multi-unit plate may comprise a stand, e.g. in the form of sidewalls or other means. The stand may have guiding structure matching the structure on the reservoir plate and the waster pad to align the multi-unit plate in only one orientation for non-error liquid transfer. In some embodiments, the reaction unit and the plate body have matched structure to enable the reaction unit to be attached onto and/or detached from the plate body.

B. Reservoir Plate

According to the invention, a device said reservoir plate, used in conjunction with the multi-unit plate for liquid transfer, comprises a single well or a plurality of smaller wells or grooves that are within plate body. There may be guiding structure at the edge of the plate matching the structure on the multi-unit plate to allow each reaction unit goes into the well or groove to transfer liquid in only one orientation.

C. Waster Pad

If appropriate a waster pad to be used in conjunction with a reaction unit, resp. a multi-unit plate is foreseen to remove liquid from at least one reaction chamber. The waster pad comprises at least one layer of liquid absorbing material, which provides a higher capillary effect then the reaction chambers; thereby it becomes possible to remove the liquid. The base may have guiding structure at the edge of its body matching the structure on the multi-unit plate for each reaction unit contacting the pad in one orientation.

D. Liquid Transfer Guider

If appropriate a liquid transfer guider is foreseen to facilitate the liquid transferring from a reservoir plate to a multi-unit plate or from a multi-unit plate to a waster pad and to eliminate orientation mistake as well as to prevent reaction units from damage. It comprises in general a base having a housing structure to hold a reservoir plate or a waster pad and an upper multi-unit plate holder that can move down along supporters fastened on the base. The holder has an opening to permit the bottom of each reaction unit on the multi-unit plate to contact a solution in a well of the reservoir plate or the absorbing layer of the waster pad when it moves towards the base.

E. Low Volume Full Spectrum Cuvette Adaptor

According to an embodiment of the invention, a low volume full spectrum cuvette adaptor is provided to hold and position a reaction unit in a light path of a spectrophotometer in order to allow light beam to pass through the reaction unit.

BRIEF DESCRIPTION OF THE DRAWINGS

The herein described invention will be more fully understood from the detailed description given herein below and the accompanying drawings, which should not be considered limiting to the invention described in the appended claims.

FIG. 10 is a perspective view of a reaction unit containing a build-in lens;

FIG. 11 is a top view of a reaction unit containing a build-in lens;

FIG. 12 is a cross-cut view of a reaction unit containing a build-in lens;

DESCRIPTION OF THE EMBODIMENTS

According to the invention, a reaction unit 1 is a device used for carrying out an experiment or an application such as analysis, reaction, assay, sampling, transfer, distribution, storage, dilution and/or extraction.

Figure 1:
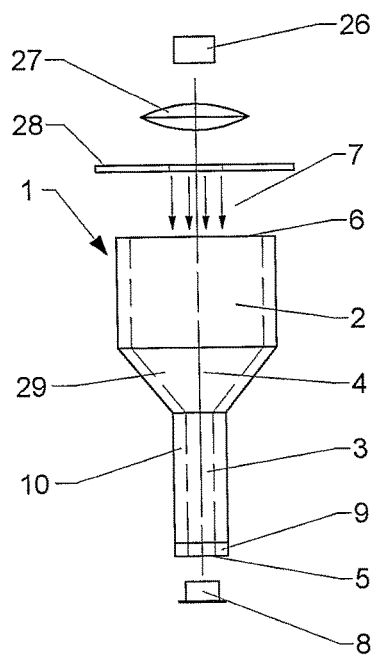
FIG. 1 is an illustration of a reaction unit and a method of its use.

FIG. 1 shows an embodiment of a reaction unit and its use. The reaction unit 1 shown here is a tubular device comprising an upper part of a non-capillarity zone 2 and a lower part of a closed capillarity reaction chamber 3. Both run length-wise along a major axis 4 of the reaction unit 1. The reaction chamber 3 is designed so as to have the radius enabling it to use capillary action to draw in enough amount of liquid to fill up a space with a volume no less than that of the lower part 3 of the reaction unit. In an embodiment the radius in the range of 0.005 mm to 1.5 mm. Other dimensions may be appropriate.

But the radius for the non-capillarity zone 2 will not have capillarity or may have weak capillarity but not strong enough to against the gravity to keep liquid in the non-capillarity zone 2. Alternatively, the non-capillarity zone may be derived from a portion of reaction chamber through chemical treatment. In such a design, only amount of liquid equaling to a volume of reaction chamber or the lower part of the reaction unit can the reaction unit take up by itself under the capillary action. A sample solution can enter through a bottom opening 5 once the bottom open structure contacts with the solution and meanwhile the air will go out of the reaction unit through the upper opening 6. The solution will stop flowing in when it reaches to the non-capillarity zone 2 because the capillary action is not sufficient to further pull the liquid in. The reaction unit 1 can then hold the same amount of solution in the reaction chamber 3 when the bottom opening 5 leaves a sample solution surface since the capillarity in the reaction chamber 3 is strong enough to against the gravity force to pull the liquid away. This capillary action driven liquid loading provides a simple, reliable and easy-to-use liquid transfer method.

A detection device e.g. such as a spectrophotometer can be used to measure analytes in the solution in the reaction chamber 3 through which light 7 from a light source 26 which passes in the shown embodiment through a lens 27 and a aperture 28 and then along the major axis 4 through the reaction unit 1. The concentration of the analytes can be derived from the optical density obtained by a detector 8. In the shown embodiment a black ring like bottom structure 9 may optionally be installed as a light guiding device to block the light passing through the reaction chamber body 10. Because no other object, but the solution, is in the light path of the reaction unit, the device can directly be used as a cuvette for extended spectrum detection (e.g. full light spectrum from UV to inferred).

Figure 2:
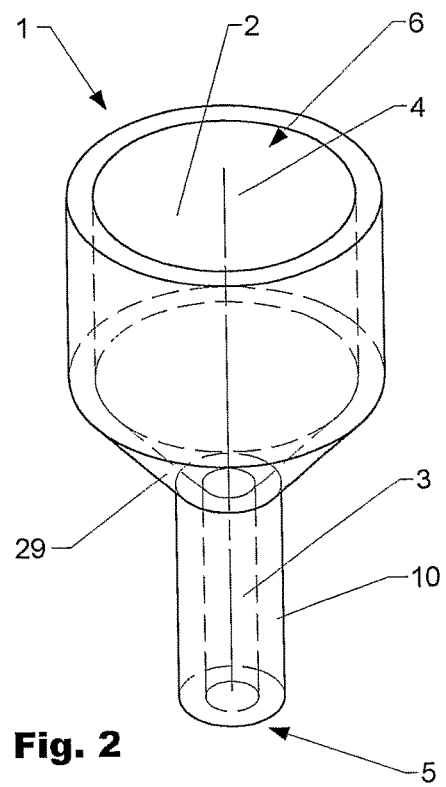
FIG. 2 indicates a perspective view of a reaction chamber.

FIG. 2 shows the reaction unit 1 of FIG. 1 in a perspective view. As it can be seen, the reaction unit 1 comprises a tubular capillary zone 3 and adjacent thereto a non-capillary zone 2. Between the two zones a transition area 29 is arranged which has in the shown embodiment a conical shape. Depending on the field of application other shapes are appropriate. As it can be seen the cross-section of the capillary zone 3 and the non-capillary zone 2 are both circular. However, in some embodiments, the cross-section of the reaction chamber 3 may have geometric patterns which are different e.g. in order to specifically increase the surface area in the chamber, to increase capillary action, to increase total volume, and/or other objectives. Depending on the field of application square, round, star-like, oval or rectangular cross-sections may provide best results.

Figure 3:
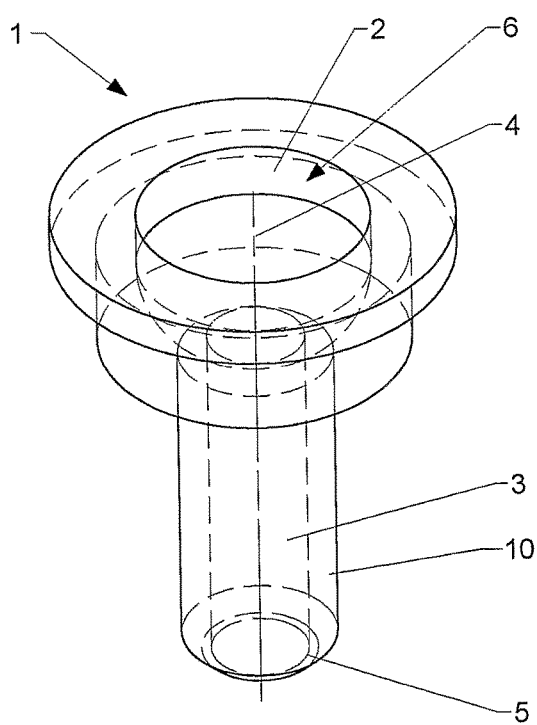
FIG. 3 is a perspective view of a reaction chamber having a U-shaped non-capillarity zone.
Figure 4:
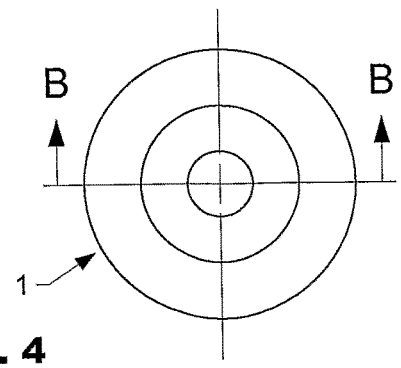
FIG. 4 is a top view a reaction chamber having a U-shaped non-capillarity zone.
Figure 5:
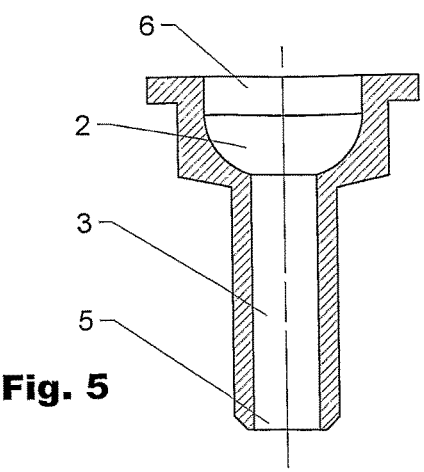
FIG. 5 is a cross-cut view a reaction chamber having a U-shaped non-capillarity zone.

FIG. 3 shows a further embodiment in a perspective view, FIG. 4 shows the same embodiment in a top view and FIG. 5 a cross-cut through along line BB of FIG. 4. As it best can be seen in FIG. 5, the transition area 29, which is arranged between the capillary zone 3 and the non-capillary zone 2 is in general U-shaped having an in general horizontal section adjacent to the capillary zone 3. Thereby it is achieved that the liquid does not remain inside the non-capillary zone, which may tend to happen with flatter angles.

Figure 8:
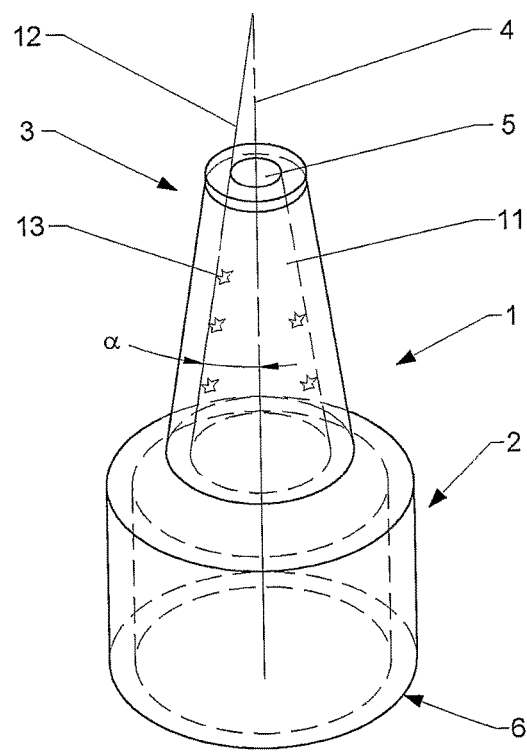
FIG. 8 is a perspective view of a reaction unit having a cone shape reaction chamber.

The dimension of the cross-section from top to bottom may be various according to applications. A cone shape reaction chamber 3 for example, as shown in FIG. 8 in an upside down view, has an inner surface 11, for example formed by rotating a straight line 12 in a desired angle α around the central axis 4, is preferred in the detection of fluorescence produced by the analytes 13 bound to the inner surface 11 of the reaction chamber 3 because the conical surface 11 can receive more light compared to a cylinder shape.

Figure 9:
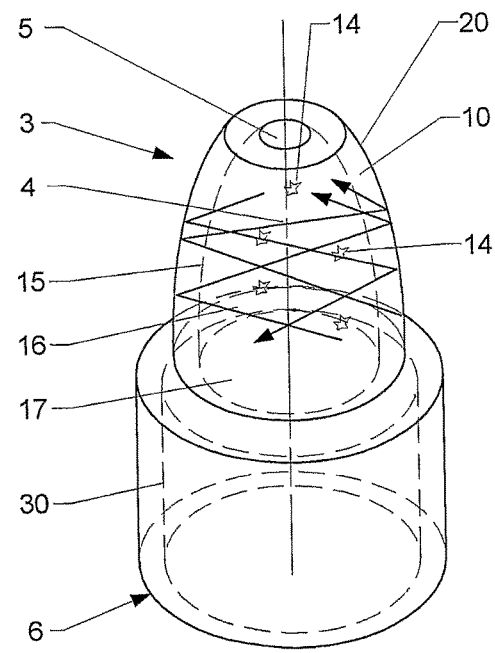
FIG. 9 is a perspective view of a reaction unit having a U-shaped reaction chamber.

FIG. 9 indicates an embodiment with an in general U-shaped reaction chamber 3 in an upside-down manner. The inner surface 11 is formed by rotating a particular curve 15 around the central axis 4. This U-shaped design directs more optical signal 16 (e.g. luminescence or fluorescence), generated by the analytes 14, towards a wider opening 17 of the reaction chamber 3.

It has been observed that the strength of the capillarity of the reaction chamber, the dimension of the reaction chamber openings and/or the liquid retention volume at the bottom, which is related to the dimension and surface features of the bottom end, may have some influence on the surface form (e.g. concave, convex and flat) of the interface between the liquid and the air. Different surface forms can be obtained through the change of a single parameter or multi-parameters in order to meet different needs. For example the dimension of the bottom end is one of the key factors to determine the retention volume of the liquid: the bigger the dimension, the more the retention volume. It is possible to change the retention volume by varying the dimension of the bottom opening and/or the thickness of the reaction chamber body at the end. It has been seen that the liquid surface at the upper opening of the reaction chamber is tend to be concave when the bottom opening is leaving the sample solution. If the retention volume at the bottom is less than that needed to convert the concave surface into flat or convex surface, the surface at the upper opening will be concave. Therefore, the desired surface forms can be easily obtained by changing these two parameters. For instance, a cone shape reaction chamber having a smaller bottom opening with gradually reducing the thickness of the reaction chamber body at the end will have minimum retention volume and can form a concave liquid surface at the upper opening which is more suitable for fluorescence measurement because the concave liquid surface can serve as a lens to diverge the parallel incoming light toward the wall of the reaction chamber. In an absorbance measurement a reaction chamber able to generate near flat surface is more suitable. In some preferred embodiments, the non-capillarity zone 2 may have cross-section geometry of circular, square or rectangular shape with a flat, V- or U-form bottom or other combinations. It can also serve as a simple light guiding structure to block light passing through the reaction unit body but the reaction chamber. For example a non-optical transparent material can be used for making or coating the whole or part of the non-capillarity zone body. For some particular applications, an inner surface 30 of the non-capillarity zone 2 may have a rotation symmetric cylindrical or a conical shape, formed by rotating a desired curve around the central axis 4. Depending on the shape, the inner surface 30 may function as a light guiding device to focus light 7, coming from a light source 26 (see FIG. 1), onto a reaction chamber 3 or direct light signal inside a reaction chamber to a detector. Alternatively of in addition a build-in lens 19, as schematically shown in FIGS. 10 to 12, may be arranged at the top of the non-capillarity zone 2 as a light guiding device. FIG. 10 shows the reaction unit 1 in a perspective manner from above, FIG. 11 the reaction unit 1 according to FIG. 10 in a top view and FIG. 12 shows a cross-cut along line AA through the reaction unit according 1 to FIG. 11.

The whole or part of the inner surfaces of the reaction unit 1 may have a highly reflective surface-coating to avoid the loss of the optical signal from passing through the body and thus to direct more light to the detector at the opening. For example as shown in FIG. 9 an outside surface 20 of an optical transparent body 10 may have a layer of silver or an other appropriate material. The optical radiation 16 produced by analytes 14 in the reaction chamber can finally escape only from the upper wider opening 17 and the lower opening 5. A detector (here not shown in detail) can then capture the optical signal 16 from these openings. The reflective surface may also have a layer of an over-coating for other objects like to protect the reflective layer, to avoid optical contamination and so on. For example when the surface of the reaction chamber has an aluminum layer, an over-layer of other material can avoid the reagents to directly contact with the aluminum surface.

The surface of the reaction unit may chemically and/or physically be treated to permit selective binding of or non-binding of target molecules based on the particular use or assay procedure (e.g. non-homogeneous assay like ELISA or homogeneous assay). By introducing a surface layer of desired materials, the functional domain of the molecule in the layer will interact with target molecules through covalent or non-covalent bonds like ionic, hydrophobic interaction, or metallic bonds, or will protect target molecules from binding. For example, the surface of the reaction chamber is coated with a layer of an antibody and the correspondent antigen in the sample will bind to the antibody and remains on the surface after removal of the sample solution from the reaction chamber. In various embodiments, preferably, the outside surface of the reaction unit or part of it may chemically be treated to form a non-wetting surface for avoiding the forming of a fluidic droplet. For example a hydrophobic outside surface will be more suitable for a reaction or assay carried out in an aquatic solution.

By using a rough surface finishing (not shown in detail), a reaction chamber 3 can largely increase its surface area so that more target molecules are able to attach to. The rough surface finishing of a reaction chamber can also increase liquid retention and form a liquid thin layer on the surface of the reaction chamber made of either hydrophilic or hydrophobic materials. The liquid layer will ease the liquid to flow into the reaction chamber especially made of hydrophobic materials and will also protect bound molecules from drying rapidly.

The reaction unit 1 is in general made out of solid materials such as metal, glass, plastic (e.g. polystyrenes, polypropylenes, acrylates or polycarbonate), rubber or others. In some applications, the reaction chamber and the non-capillarity zone can be made of different materials (any kind of difference e.g. in composition, structure, color and so on) or made of one material and treated one of them with another material because they have different functions and need to meet different requirements such as the feature of capillarity, chemical resistance and so on. For example the whole body of a reaction unit may be made of hydrophobic plastic and the surface of the reaction chamber can be coated with a hydrophilic polymer containing a functional domain to which a protein or oligo nucleotide can attach.

Conventional technologies for manufacturing the reaction unit include micro-machining, electrospark discharge machining (EDM), or chemical etching.

Alternatively, the reaction unit can be cast using a polymer or resin. The reaction unit can also be made through assembling different parts together or fusing two half-reaction units together. For example, to cast a reaction unit containing a silver layer within the body of the reaction chamber, a desired hollow tube with a silver layer on its out surface can be immobilized within the casting mold of the reaction unit. The chemistry of the hollow tubes and polymer will ideally be chosen such that a permanent bond will form between the outside hollow tube and the resin or polymer that is cast. The inner surface of the hollow tubes will then make up the reaction chamber. In such a way, many different devices such as electrodes, optical fiber and so on can easily be incorporated into the reaction unit.

Figure 13:
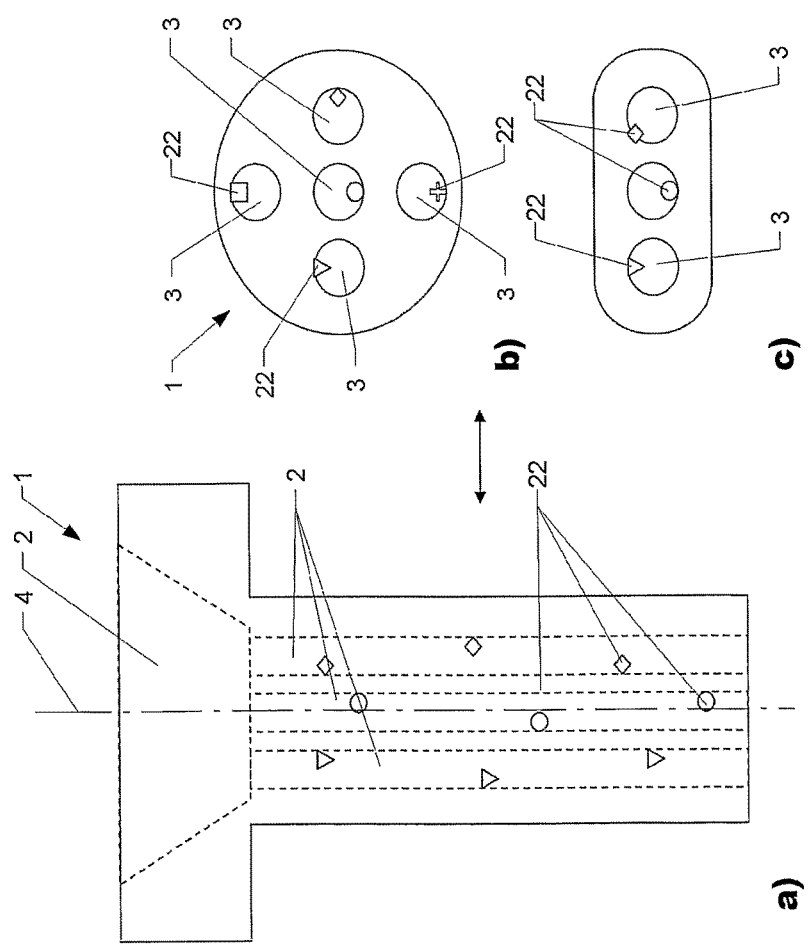
FIG. 13 is an illustration of a reaction unit for multiplexed detection with cross-section view of two examples.

According to different applications of the invention, the reaction unit can have various forms combined with additional feature, structure, and device. FIG. 13 shows a reaction unit 1 for multiplexed detection in a side view (FIG. 13a) and in top views (FIGS. 13b and 13c). The reaction unit 1 comprises several reaction chambers 3, each containing an antibody 22. The reaction chambers are arranged in general parallel to each other. After loading a sample containing multi antigens, the antibodies 22 in the reaction chambers will only capture its target antigen from the sample solution. With additional reagents, the reaction chambers that contain their target antigens can produce optical signal which can be recorded by a device for example CCD camera.

Embodiments of a reaction unit 1 schematically shown in the drawings may contain any kind of electrodes (not shown in detail) adapted to the reaction chamber for detecting electro-signal related to a chemical reaction, molecule interaction, cell activity and so on. For example, it can detect an electrochemical reaction such as redox reaction. Such a reaction unit may also be used to force liquid flowing and charged molecules moving, to raise temperature, to induce electrochemiluminescence and so on inside the reaction chamber. For example, applying an alternating electric field can force charged molecules moving back and forth inside the reaction chamber to facilitate molecule diffusion, to speed up the reaction or to mix solutions. Electro-osmotic flow phenomenon can also be used to mix solution. A micro ultrasound device (not shown in detail) may also be incorporated into the reaction unit for mixing solution, speeding up reaction, raising temperature and so on. According to an embodiment of the invention, optical fiber (not shown in detail) may be incorporated in the reaction chamber for example to generate evanescence that can then excite fluorophor labeled molecules bound to the molecule that is immobilized on the optical fiber surface for fluorescence detection. The optical fibers may also function as an optical guiding device to direct light in and/or out of the reaction chamber for the measurement of optical density, fluorescence, luminescence and so on. The reaction unit 1 may be used as a device for chromatography, electrophoreses and so on. For example a porous material may be filled in the reaction chamber for chromatography and synthesis. In order to avoid the loss of the porous material from the bottom opening of the reaction chamber, a bottom structure with tiny hole(s) may be used.

Figure 14:
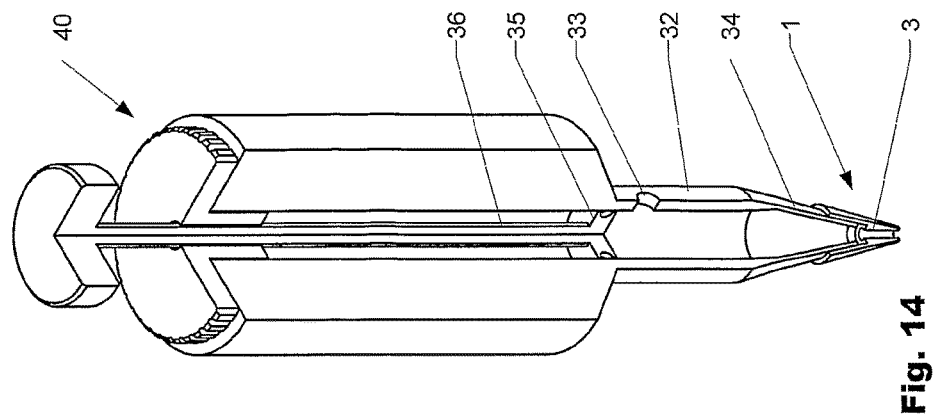
FIG. 14 shows a self-transfer-in low volume manual pipette.

FIG. 14 shows a pipette 40 with a reaction unit 1 according to the invention in a perspective manner. The pipette 40 and the reaction unit 1 are shown in a cut view such that their inside is visible. The reaction unit 1 can be used for a liquid transfer device, for example a low volume pipette, where the reaction unit, as a tip of the pipette, can quantitatively take up liquid by itself from a liquid reservoir using capillary action and a dispense device can then push the liquid to a receiving receptacle. Amount of liquid to be transferred is defined by the volume of the reaction chamber in a reaction unit. The pipette 40 comprises: a) a housing 31, a cylinder 32 including two cylinder ends and open structure 33 (opening), with one end positioned within the housing 31 and the other end extending from the housing to form a pipette tip holder 34, a piston 35 that moves within the cylinder between up-limit and down-limit, when the piston located at the up-limit, the inner space of the cylinder is also connected to the atmosphere through the open structure 33 on the cylinder, while the piston moves down and passes the open structure the air in the inner space of the cylinder can only go through the open structure of the pipette tip holder 34 thus to dispense the liquid in the pipette tip to a receiving receptacle, and a plunger 36 that drives the piston; b) a disposable pipette tip (reaction unit) 1 can be attached to the end of the tip holder to take up by itself as well as retain the liquid to be transferred. This tip can be removed from the tip holder, disposed of, and replaced with a new tip.

The pipette may be configured to transfer liquids by automated or manual actuation of the pipette. Automatically operated pipettes may include a motor for actuating the plunger to move the piston within the pipette cylinder for liquid transfer. Manually operated pipettes require the pipette user to apply force to the plunger head (38), usually with a thumb, to actuate the piston.

Since the taking-up volume is solely determined by the tip itself, the liquid transfer device does not need a very accurate, expensive, complex and difficultly manufacturing piston-and-cylinder unit. Besides, the device will be accurate, need no calibration, have no manmade transfer volume difference, require less finger movement, have no temperature caused pipetting volume change due to the warm hand, and so on. Furthermore, the device can be used for non-volatile fluid as well as highly volatile fluid because the air pressure in both sides of the liquid to be transferred will always keep the same at the taking-up position. It may not be necessary to have an open structure on the cylinder wall for non-volatile fluid because the tiny amount of fluid taken up by the tip will not build a pressure inside cylinder high enough to interfere the tip to take up the fluid quantitatively. The existing pipette may also be used as a dispense device.

Figure 6:
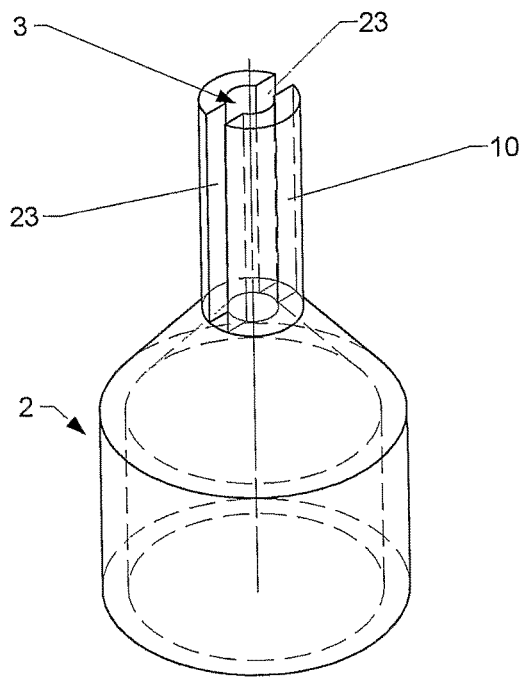
FIG. 6 is a perspective view of a reaction unit having an opened reaction chamber.

Because the reaction unit can take up and hold quantitative amount of liquid, it can be used as devices for sampling, transfer, distribution, dilution, extraction, storage and so on. An opened capillarity reaction chamber as e.g. shown in FIG. 6 may be a preferable device for dilution and extraction because the liquid in the reaction chamber can directly contact with another one through the open structure 23 (gap) in body 10. To achieve a defined dilution, the quantitative amount of first solution in the reaction unit can easily be mixed with a desired volume of second solution in a well or tube. For extraction, the two liquids should be insoluble with one another and the reaction unit should generate capillarity strong enough to hold one of them in the reaction chamber. During extraction, the liquid in the reaction chamber will stay there and should not be replaced by another one. For example, a hydrophilic reaction unit can be used for taking up a hydrophilic sample solution and then can be immerse into desired hydrophobic solvent in a container for extraction. A redistribution of analytes occurs between the two solutions and will finally reach equilibrium.

Figure 7:
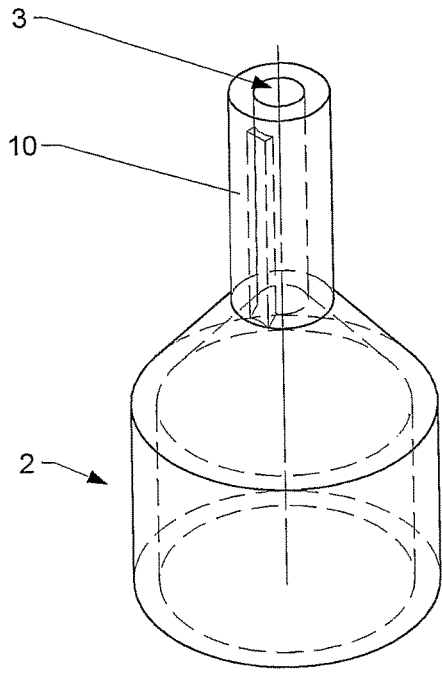
FIG. 7 is a perspective view of a reaction unit having a closed reaction chamber.

A closed reaction chamber 3 as schematically shown in FIG. 7 is a suitable device for direct storage of samples. In order to prevent stored frozen sample (e.g. biological sample, compound and so on) from falling off, the reaction chamber can be designed so that the bottom has a smaller dimension than the top for example V or U forms. Alternatively, a bottom structure with a smaller dimension or different cross-section can be used to hold the sample. Further, the bottom structure may be made of a hydrophobic material and is designed to have a dimension of the open structure big enough to permit hydrophilic liquid passing through but will avoid the solution contacting a bottom sealing membrane because the non-wetting bottom structure will not pull the solution to fill up its space due to the surface tension of the liquid.

A micro sensor may also be adapted to the reaction chamber for measuring temperature, pH, target molecules, and so on.

With the development of nano-technology, more and more new and useful devices can also be adapted to this invention.

Multi-Unit Plate

Figure 15:
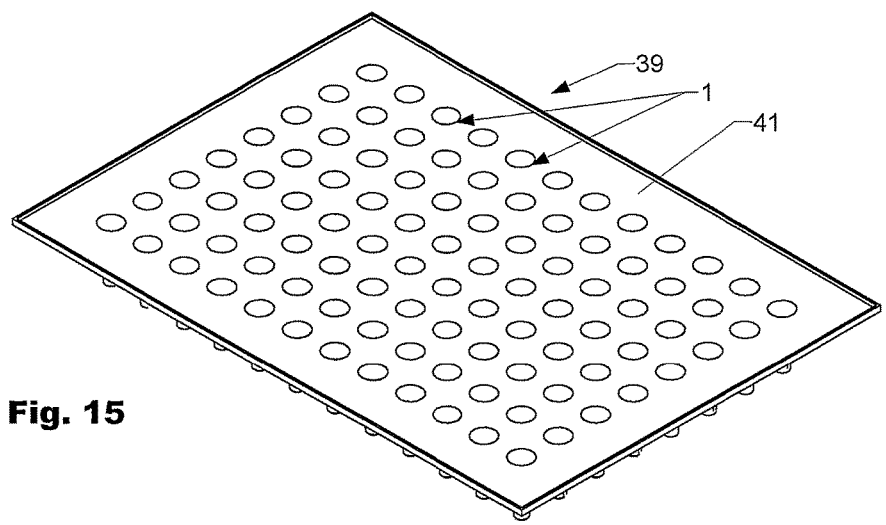
FIG. 15 is a perspective view of a multi-unit plate.
Figure 16:
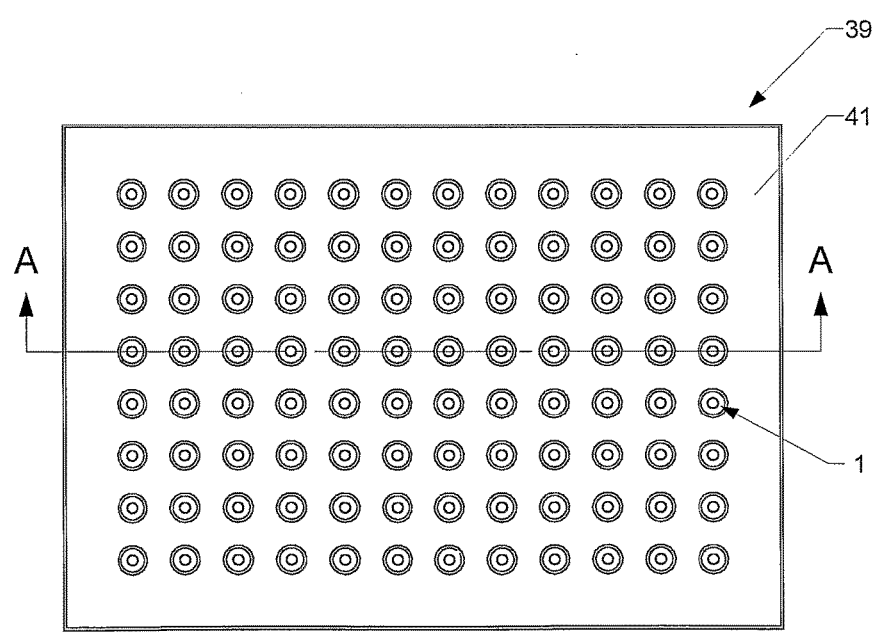
FIG. 16 is a top view of a multi-unit plate.
Figure 17:
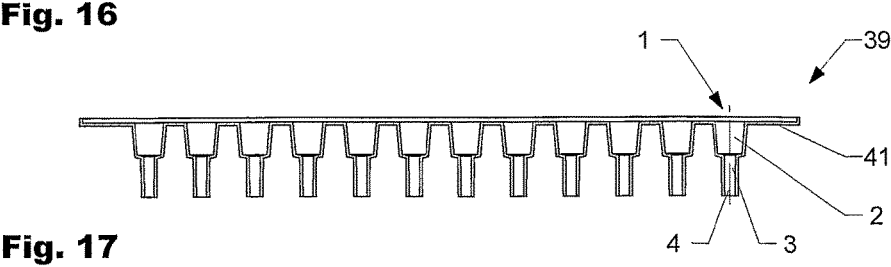
FIG. 17 is a cross-cut view of a multi-unit plate.

According to the invention, parallel experiment of any kinds of above applications may be carried out in a number of reaction units on a multi-unit plate. FIG. 15 shows a perspective view of a multi-unit plate 39 in perspective view, FIG. 16 in a top view and FIG. 17 in a cross-cut view along line AA of FIG. 17. Several reaction units 1 are integrated within a plate body 41. The axis 4 of each reaction unit 1 is in general perpendicular to the plate body 41. The multi-unit plate is adapted for use in conjunction with a reservoir plate, e.g. for example a 96-well format (not shown in detail) plate and waste pad for liquid transfer. At the edge of the plate body, there may stands protruding (not shown in detail) that are sufficiently high to avoid the bottom of the reaction unit to contact a surface on which the multi-unit plate is positioned. The stand may contain guiding structures (not shown in detail) matching that on the reservoir plate and the waster pad to align the multi-unit plate in a desired orientation with the reservoir plate and the waster pad for non-mistake liquid transfer. The multi-unit plate can be made of any solid materials such as metal, plastic and glass, without limitation by way of example. A multi-unit plate frame (a multi-unit plate without reaction unit) and the reaction unit may be made separately then assemble together. Numerals structure can be used to fix the reaction unit in the opening on the multi-unit plate frame. For example, in an embodiment, screw and nut structure is used and the plate frame serves as a rack for the reaction unit. This designing may be more suitable for sampling, storage, dilution, transfer and so on. The multi-unit plate frame and the reaction unit can also be made in whole by casting. In some cases, part of the reaction unit may be made together with a plate body then assemble together. For example the non-capillarity zone can be made in one plate body and the rest part of reaction unit is made together with a multi-unit plate frame.

Dilution Plate

According to the invention, a dilution plate is a particular use of the multi-unit plate to make the dilution much easy and fast. In an embodiment dilution units (or reaction units) with defined volume can be fastened on a plate body in a desired format based on the demands. For example the dilution unit in each column from A to H has a volume of 1, 2, 3, 4, 5, 6, 7, and 8 micro liters. A grooved reservoir plate in column format is used and each sample is loaded in each grooved well. Dilution units in each column will take up a serial amount of each sample. The sample can then be transferred for example by centrifugation to a welled reservoir plate where wells in each column from A to H will get 1, 2, 3, 4, 5, 6, 7, and 8 micro liters of the sample. In such a way, a serial of dilution of standard and samples in an assay can be easily done in a single step from a standard or samples without many steps of pipetting.

Liquid Transfer Array Device

Figure 18:
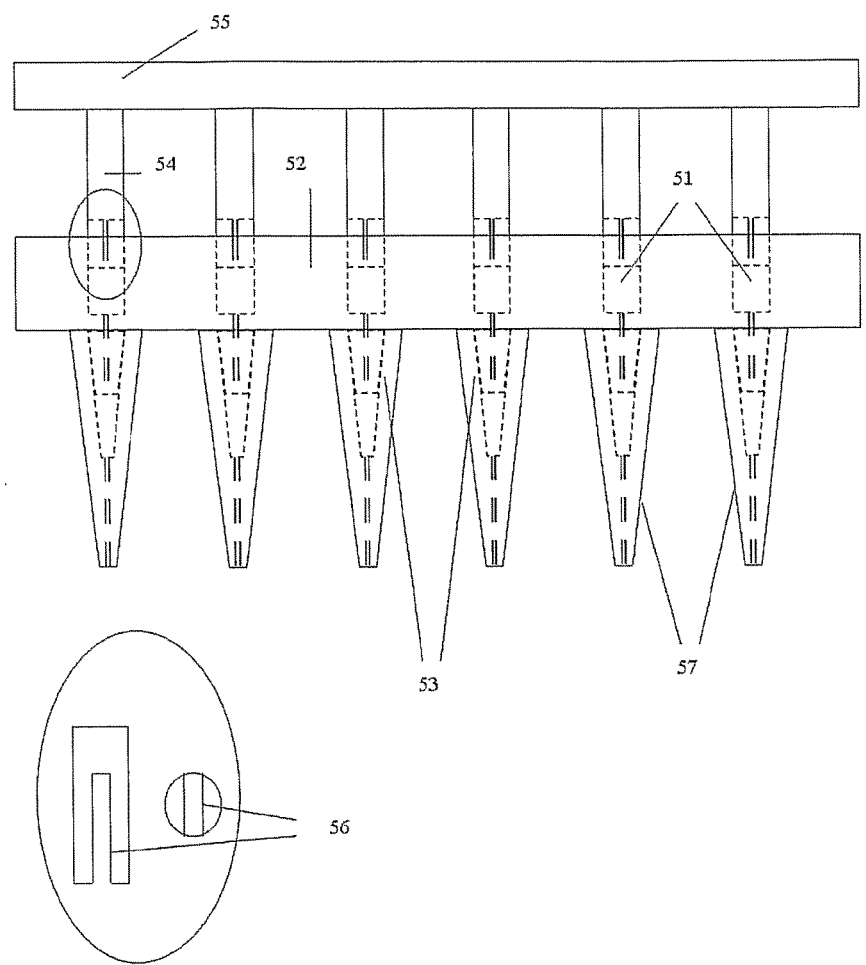
FIG. 18 shows an illustration of a liquid transfer array having piston-and-cylinder system.

According to an embodiment in FIG. 18 of the invention, liquid transfer array device comprises: a) a number of cylinders 51 within an array plate body 52 with one end project from the body to form a holder 53 for a pipette tip; b) a number of pistons 54 of which one side is fixed on a driving plate body 55 and another side containing a slot 56 can move within the cylinder; c) a number of quantitative liquid self-transfer-in pipette tips 57 can be attached to the holders. When the driving plate is at the liquid taking-up position, the slut of the piston connects inner space of the through-hole to the atmosphere so the attached tips can take up quantitative amount of liquid from a reservoir by itself without the influence of the air pressure otherwise built up inside cylinder. The liquid can be dispensed into a receiving receptacle when the driving plate pushes the piston further after the slut is within the cylinder.

Figure 19:
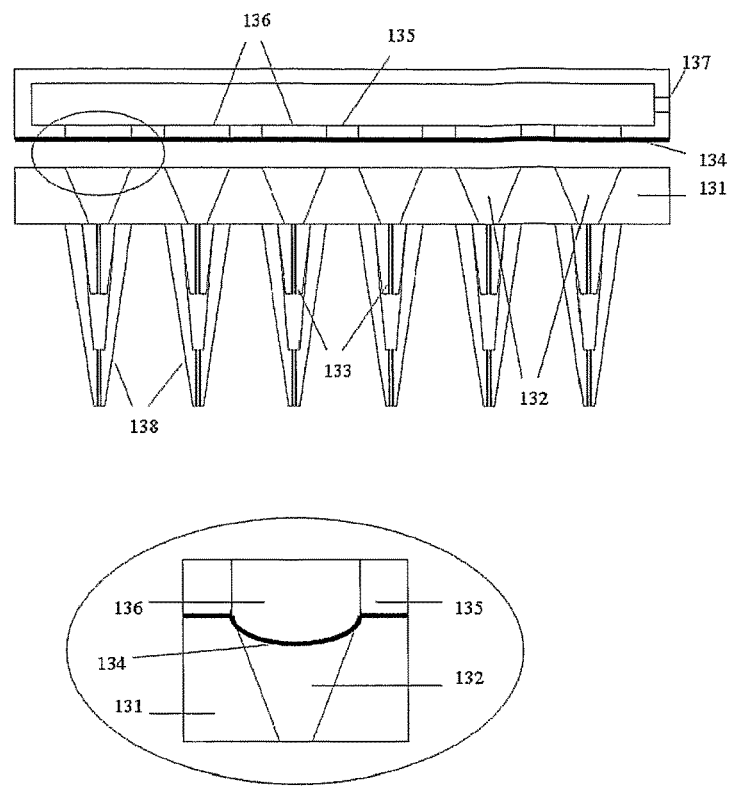
FIG. 19 is an illustration of a liquid transfer array having a membrane-based system.

A membrane-based system that can function as the above piston-and-cylinder system to produce positive pressure. FIG. 19 is an illustration of a liquid transfer array device using a positive pressured gas to fulfill the liquid transfer from the tips to a receiving multi-well plate. The device comprises an array platen 131 with a number of through-holes 132 where the bottom ends form the pipette tip holders 133, an elastic membrane 134 attached to the bottom platen 135, containing of openings 136 in same format of the array platen, of a driving force producer with a gas inlet/outlet 137. When at the taking-up position, the upper through-hole end of the array platen does not contact the membrane and therefore the through-hole is also open to the atmosphere at the upper end. When at the dispensing position illustrated inside the cycle, the array platen and the driving force producer are brought together and the membrane in between will tightly contact the upside of the array platen to seal the upper ends of the through-holes 132. Pressured gas is then allowed to flow into the driving force producer to push the membrane 133 of the openings 136 bowing towards the through-hole 132 of the array platen to push the liquid out of the tip 138. The pressured gas can be obtained by a mean of pressured gas tank or pumps. This membrane-based system can also be used directly for expelling of the liquid from the multi-unit plate or dilution plate when they are used as the array platen 131 and the tips 138.

Reservoir Plate

The reservoir plate may have many types like a plurality of wells, grooves, grid like grooves or a big flat well. These plates may be fabricated from a variety of solid materials of metal, glass, or plastic, without limitation by way of example. The surface of the plate may chemically be treated to avoid the binding of the reagents or to expel the solution according to the applications. The dimension of the liquid reservoir plate will permit the bottom opening of each reaction unit to contact the solution in the well of the reservoir plate. There may be guide function structure matching the structure on the stand of the multi-unit plate for guiding the reaction units go into the correspondent locations like wells or grooves.

Wells on the reservoir plate is arranged in a format correspondent to that of the reaction unit on the multi-unit plate. The well shall be big enough for the project part of the reaction unit to go into it. Therefore, the bottom opening of the reaction unit can contact the liquid in the well to take up quantitative amount of liquid into the reaction chamber.

Figure 20:
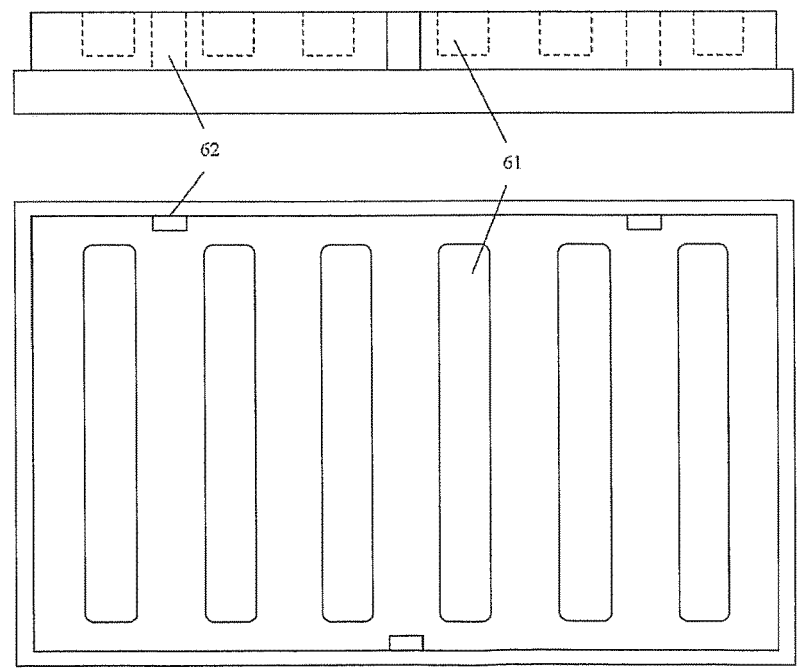
FIG. 20 is an illustration of a reservoir plate with groove well in column format.
Figure 21:
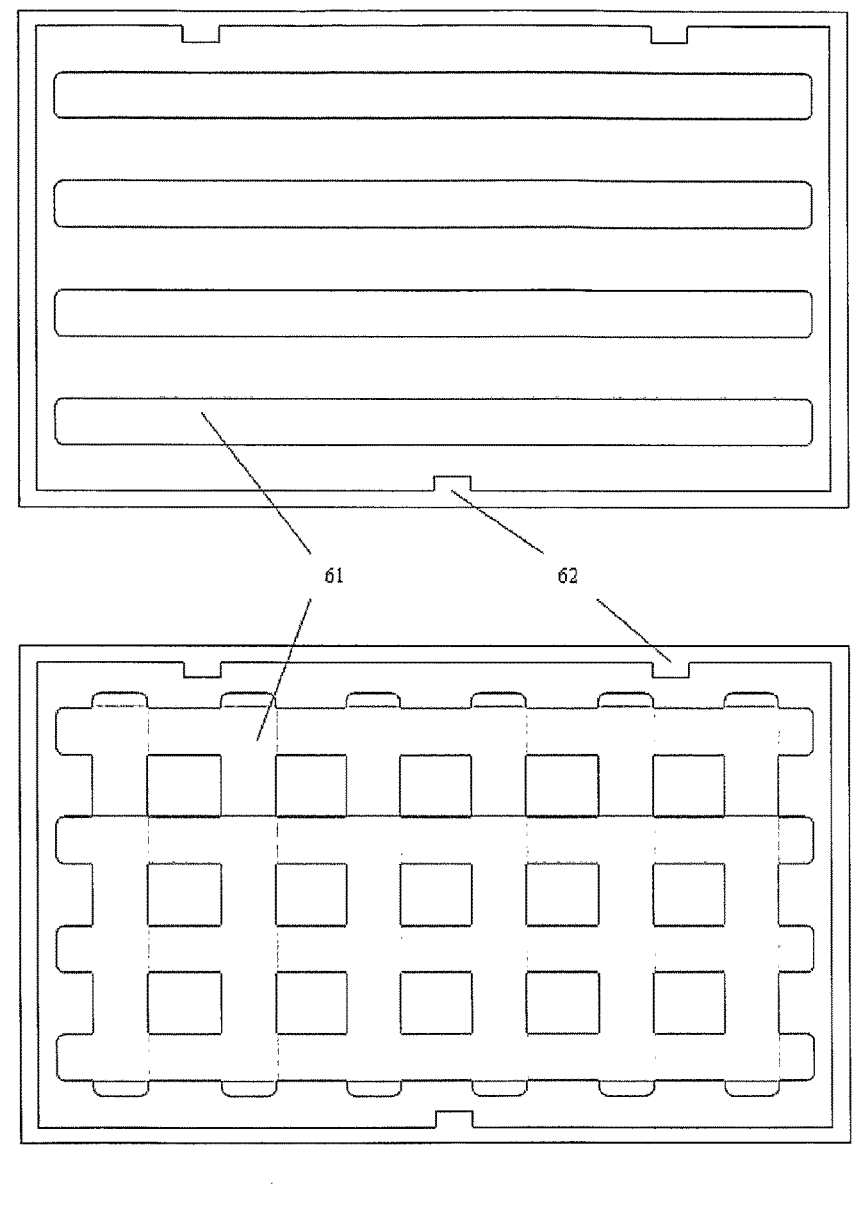
FIG. 21 is top views of reservoir plates with groove in row and grid format.
Figure 22:
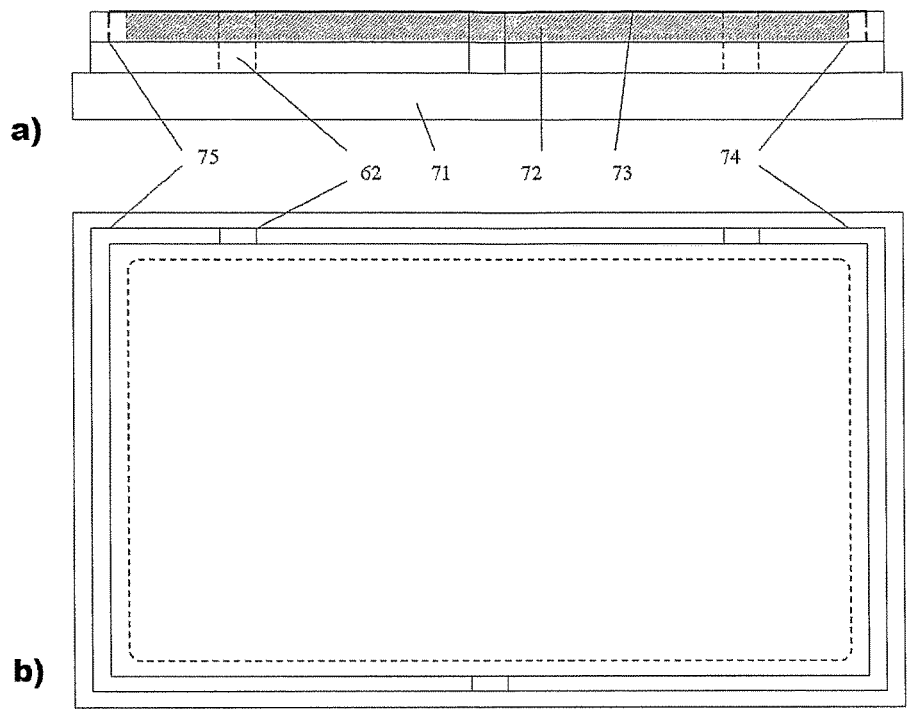
FIG. 22 is an illustration of a waster pad.

The grooved well of the reservoir plate shall have dimension and format that permit the bottom opening of reaction unit to contact the liquid in the groove. The groove formats and length are designed for different applications in order to reduce the times of pipetting. FIG. 20 is an embodiment of a grooved reservoir plate in a full-length column format. The groove 61 is long enough to permit all reaction units in one column of the multi-unit plate to go into the same groove. There is guiding structure 62 at the edge of plate matching the structure on the stand of the multi-unit plate for guiding the reaction units go into the correspondent grooves and the reaction units in each column will get the same sample. If a grooved reservoir plate in a full-length row format as shown in FIG. 21 is used to introduce different detection reagents in a row-wise, the reaction units in each row will receive the same detection reagent. In such a way, one sample can simultaneously be tested by several different reagents. The grid like grooved reservoir plate FIG. 22 is for a special case of the grooved reservoir plate for filling up all reaction units with same solution. Although it can be replace by a big flat welled reservoir plate the grid like groove type plate needs less solution for performing the liquid transfer.

Waster Pad

FIG. 22 shows an embodiment of a waster pad, The waster pad comprises a base 71, an absorbing layer 72 having very strong capability to absorb liquid and a surface layer 73 that protects the under layer and permits liquid to pass through. The absorbing layer is sat in a space formed by wall like structure 74 on the base. The above surface layer is fastened by a frame structure 75. There may be guiding structure 62 matching the structure on the stand of the multi-unit plate for guiding the reaction units to contact the surface layer in a desired orientation.

In other variants the base may contain draining structure under the absorbing layer and an opening to permit connect to a device like vacuum pump to suck the liquid out of the absorbing layer for keeping the layer functional when a large amount of liquid needs to be removed for example in case of top loading.

Figure 23:
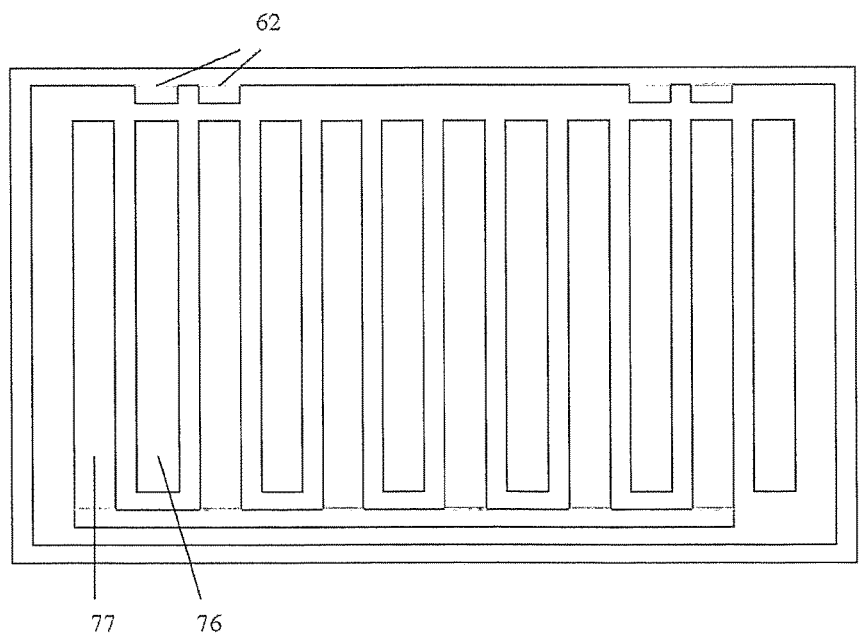
FIG. 23 is a top view of a washing plate with reservoir grooves and waster pad strips.

FIG. 23 indicates an embodiment of a waster pad designed as a plurality of strip pads 76 with a groove like reservoir 77 in next to further ease some procedures for example to repeat washing the reaction chamber. There may be guiding structures 62 matching the structure on the multi-unit plate for guiding the reaction units go to the correspondent locations like grooves or strip pads. Therefore, the filling-up reaction chamber and the removal of the washing buffer can be carried out on the same plate.

Liquid Transfer Guider

Figures 24, 25:
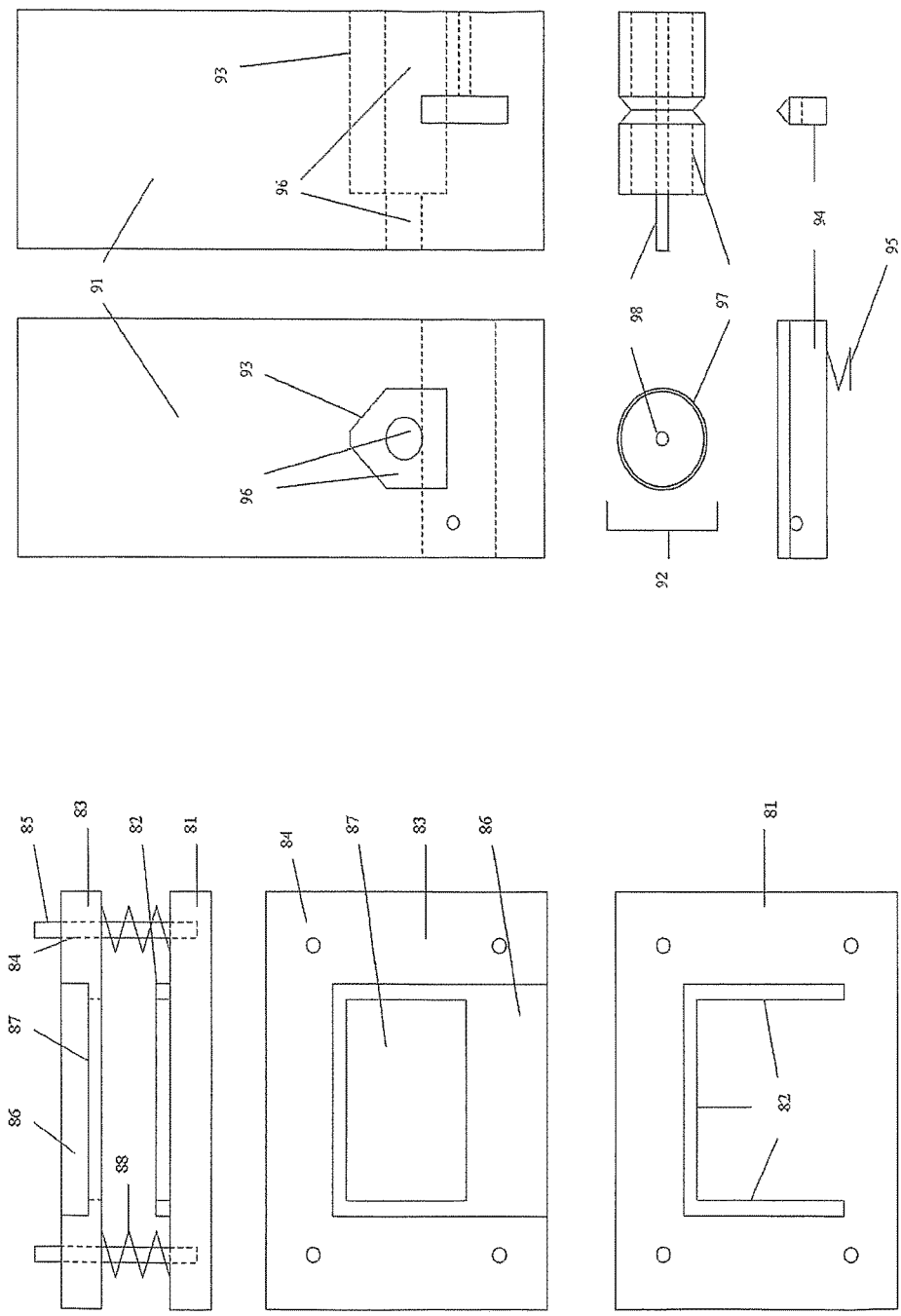
FIG. 24 is an illustration of a liquid transfer guider.
FIG. 25 is an illustration of a low volume full spectrum cuvette adaptor and a cuvette.

According to an embodiment of the invention, the liquid transfer guider in FIG. 24 comprises a base 81 having three-side wall structure 82 to house a reservoir plate or a waster pad on the base and an upper multi-unit plate holder 83 that can move down, guided by holes 84, along supporters 85 fastened on the base 81. The multi-unit plate holder 83 contains a groove structure 86 permitting a multi-unit plate to slide in and out along the groove structure. An opening structure 87 of the multi-unit plate holder allows the bottom of each reaction unit on the multi-unit plate to contact the solution in the well of the reservoir plate or the absorbing layer of the waster pad when it moves down towards the base. Spring structure 88 is installed between the base and the holder having two functions. One is to protect the holder from moving too close to the base resulting damage of the multi-unit plate and another is to push the holder back to its home position so that the reservoir plate or waster pad can be slide in and out of the base.

Low Volume Full Spectrum Cuvette Adaptor

According to an embodiment of the invention, a low volume full spectrum cuvette adaptor 91 as shown in FIG. 25 can be used in conjunction with a capillary cuvette 92 or a reaction unit as an ultra-micro cuvette of a conventional spectrophotometer. The adaptor comprises a V groove 93 and a lever 94 with a spring 95 in a through channel 96. A position-body 97 of capillary cuvette can be fixed in the channel through the V groove and the lever. Thus the capillary tube 98 is positioned so that when the adaptor is put into the cuvette holder of a spectrophotometer the light will go length-wise through the capillary tube from one end to another. The length of light path can be varied by changing the length of the capillary or controlling the loading volume of sample. The capillary cuvette is suitable for full spectrum detection because it is open at both ends.

B.—Methods of Use

According to the invention, the methods for carrying out experiment comprise: a) providing a device said a reaction unit adapted to take up by itself into, through the bottom open structure, and hold in the reaction chamber quantitative amount of liquid under capillary action as described above; b) quantitatively transferring into and/or out of the reaction chamber with sample, reagents, buffers and so on; c) detecting signal of spectroscopy, optical density, fluorescence, luminescence, electric potential, electrical conductivity, pH, temperature, and so on. Based on the different application, some steps may need repeat once or several times.

To transfer quantitative amount of liquid into or from a reaction unit can be carried out with the methods as the follows.

For quantitative full loading of the reaction chamber one can simply lower down the reaction unit till the bottom open structure (9) under the surface of the liquid. The liquid will spontaneously flow into the reaction chamber (3) under the capillary action and will cease flowing once the front of the liquid reaches at a position between the reaction chamber and the non-capillarity zone (2) because the dimension and/or geometry and/or surface character of the reaction chamber and the non-capillarity zone are different enough for capillarity to fade away. The amount of the liquid flow into the reaction unit is equal to the volume of the reaction chamber and this amount of liquid will contained in the reaction chamber when the bottom open structure leaves off the surface of the liquid.

It has been observed that the surface of a reaction chamber may need to be pre-wetted by liquid to form a thin layer of liquid in order to fully load the reaction chamber depending on dimension, geometry, surface character and material of the reaction chamber. Introducing a mechanical vibration process during the loading of liquid can overcome partially filling the reaction chamber. For example, sometime a reaction chamber made of hydrophobic materials e.g. polystyrene cannot be filled up fully because of incompletely pre-wetted. Therefore the mechanical vibration can be used to force the liquid to flow into the reaction chamber and to wet the surface it passes through. The liquid will finally fill the reaction chamber due to the capillary force. The mechanical vibration process may also be critical for fully loading a totally dried reaction chamber made of hydrophilic materials such as glass in a limited time.

Quantitative partial loading is performed by contacting of the bottom open structure to a desired amount of liquid on a non-wetting surface or well, which is not enough to fully fill up the reaction chamber. Further, several quantitative partial loadings can be done by repeating the above quantitative partial loading procedure when total amount of liquid does not exceed the volume of the reaction chamber.

Alternatively, addition of the quantitative amount liquid to the non-capillarity zone (top loading) or reaction chamber can also be used for a full and partial loading. Furthermore, the reaction chamber may contain dried reagents. So the reaction can start right after a sample introducing into the reaction chamber without many partial loading steps.

Total amount of liquid in the reaction chamber can be empted by the capillary action through the direct touching of the open structure (9) of the reaction unit to a surface of dry or wet absorbing material(s) having much stronger capillarity than the reaction chamber for example filter paper for aquatic solution. Alternatively, the liquid can be removed through changing the air pressure to force the liquid into the non-capillarity zone and sucking off by a device for example pipette. Vacuum, centrifugation or pressured air can also drive the liquid out of the reaction unit.

Quantitative partial amount of liquid can be removed from the reaction unit through air pressure change to force the liquid into the non-capillarity zone and sucking off the desired amount from the reservoir or directly suck off the quantitative amount from the reaction chamber by a liquid transfer device for example pipette. Alternatively, quantitative amount liquid can be removed from the reaction unit by transferring liquid onto a wettable surface through spotting. By selecting desired wettability of surface material, one can control the transfer amount for each spotting.

It is possible to replace first liquid totally and quantitatively by second liquid. One can add second liquid to the non-capillarity zone (2) with at least one volume of the reaction chamber when the bottom opening (5) of the reaction unit contacts the surface of the second liquid. The second liquid will push the first liquid out off reaction chamber to replace the old one.

To replace first liquid partially and quantitatively one can add second liquid in a desired volume to the non-capillarity zone when the bottom opening of the reaction unit contacts the surface of the first liquid. The second liquid will push the first liquid out off reaction chamber in the same amount.

In order to mix the liquid in the reaction chamber one can apply an oscillation of air pressure on the open structure of the reaction unit. The oscillation of air pressure shall force the liquid vibration in the reaction unit. For example the liquid first moves towards the non-capillarity zone and then moves back to its original position. Alternatively, an alternating electric field can also be applied to force molecules moving back and forth in the reaction unit containing electrodes for the mixing of the liquid. A reaction unit containing a micro ultrasound device can also be used to mix the liquid. Further, a mechanical vibration mixer or sound wave producer can be used for the above purpose as well.

A number of detection devices (e.g. spectrophotometer, fluorometric spectrophotometer, CCD camera, electric meter and so on) can be used for recording the signal in the reaction chamber. The build-in devices like electrodes, optical fiber and so on may ease of the signal detection.

In another embodiment, the methods for carrying out high throughput experiment comprise: a) providing a multi-unit plate having multiple reaction units adapted to take up by themselves into through the bottom open structure and hold in the reaction chamber quantitative amount of liquid under capillary action as described above; b) quantitatively transferring into and/or out of the reaction chamber with sample, reagents, buffers and so on with other devices such as liquid reservoir plates, waster pad and optionally liquid transfer guider; c) detecting signal of spectroscopy, optical density, fluorescence, luminescence, electric potential, electrical conductivity, pH, temperature, and so on. Based on the different application, some steps may need repeat once or several times.

With the help of the guiding structure on the sidewall stand between the multi-unit plate and liquid reservoir plates or waster pad or using liquid transfer guider if no such structure available, it can be very easy with capillary action to load of liquid into the reaction units in a correct orientation by dipping the reaction units to their correspondent wells or grooves of liquid reservoir plates or to remove the liquid from the reaction units by contacting of the bottoms of the reaction units with the surface of the waster pad. Repeating the above procedures or several partial loadings, samples and different reagents can easily be introduced quantitatively into the reaction units for the reaction, analysis or assay.

The groove plates are preferred for a multiplexed detection with several samples. For example each grooved well in column format plate contains a sample from each patient while each grooved well in row format plate has reagents for each particular analyte. Therefore, the reaction units in each column will be loaded with same sample and then the samples can react with each particular reagent in a row-wise. In such a way, each sample can obtain several results simultaneously.

A plate reader, CCD camera or many other detection devices can be used to read the signal from the multi-unit plate.

In a further embodiment, the methods for carrying out sampling, transfer, dilution, extraction and storage comprise: a) providing a device having one or multiple reaction unit(s) adapted to take up by itself/themselves into through the bottom open structure and hold in the reaction chamber(s) quantitative amount of liquid under capillary action as described above; b) quantitatively taking up liquid sample into the reaction chamber optionally with other devices such as liquid reservoir plates and liquid transfer guider; c) dispensing or introducing onto a surface or a membrane or into a well plate for liquid transfer or for dilution.

Because the reaction unit is also a quantitative capillarity liquid handling device, it makes sampling, transfer, dilution and storage much easier due to the features and diverse variations of the reaction unit and liquid reservoir plates. For example taking-up quantitative amount of sample can simply be done by dipping the reaction unit open structure into the sample. The sample can then dispense onto a surface by direct contact or introduce into a well by centrifugation for dilution or storage or other purpose. With an open reaction chamber, it may just need to stir the reaction unit in the well for the dilution or for extraction. The reaction unit may also be used directly for storage of a sample, optionally with sealing membrane or caps.

C.—Potential Applications

The invention, according to an embodiment, provides a parallel and/or multiple experiment platform for high throughput that can be used for low volume assays to ease liquid transfer procedure through capillary action and facilitate the reaction and may be employed for experiments of biological, biochemical, chemical or physical analysis, reaction and assay. It also provides devices and methods for sampling, storage, transfer, extraction and dilution of biological, biochemical or chemical samples.

Although there are numerous of analysis, reactions and assays, they can basically be divided into two types: homogeneous and heterogeneous. The homogeneous one can be carried out in the reaction unit just by taking up solution of reaction component sequentially or premixed. The heterogeneous one involves reaction components in different phase. For example in a solid-phase assay one of the reaction components may be immobilized on the surface of the reaction chamber. The immobilized reaction component usually interacts with other target components in the reaction solution. Signals will be generated by some reaction components if they present together in the reaction chamber and then can be detected by one of detection methods known in the art. The opened reaction unit is favorable to some heterogeneous reactions in which the two phases are for example liquid and liquid or liquid and gas because the reagents in the opened reaction chamber have more surface area to contact other reagents in another phase.

One can use the multi-unit plate to perform immunoassays. For example in ELISA, a protein sample is loaded into the reaction unit. An over-night 4° C. or a few hours 37° C. incubation will allow the protein to immobilize to the surface of the reaction chamber through physical interaction. Alternatively, the protein can be immobilized through a chemical reaction such as hydroxysuccinimide groups, which bind amine moieties on protein. After removal of the non-bound protein by several washes a milk powder solution for example is used to block the area where can further absorb protein. An enzyme labeled detection antibody then replace the milk powder solution and it will bind to the target protein on the surface of the reaction chamber. A substrate solution will be loaded for color development by the bound enzyme labeled detection antibody after completely removal of the free one by several washes of the reaction chamber. A micro-well plate reader reads the optical density at the wavelength with a maximum absorption of the substrate or product.

The sandwiched ELISA with electrochemiluminescence technology can also be performed in reaction units containing electrodes of which the working electrodes are coated with streptavidin. An analyte in a sample is sandwiched between biotinylated capture antibody and ruthenylated detecting antibody by consequently loading and removal of correspondent reagents or sample and washing in between. With the application of electrical potential in the presence of tripropylamine (TPA), the immuno-complex bound to streptavidin will generate electrochemiluminescence signal that can be captured by photomultiplier tubes (PMT's) reader.

Fluorescence polarization (FP) is a well-known technique for the study of biological interactions and is frequently used in the high-throughput screening (HTS) of potential new drug targets. It can be easily adapted to the multi-unit plate for performing the screening. For example, the FP assays can be performed in the reaction units using CyDye-labeled ligands to compete for the receptors with testing compounds. Upon the binding of CyDye-labeled ligands to the receptors, the PF value increases because of the slower rotation of the receptors. When the testing compound is able to bind to the receptor at the same binding site of the CyDye-labeled ligand, it will compete for the site with the CyDye-labeled ligand and causes the PF value decreasing due to less CyDye-labeled ligand and the receptors complex formed. Therefore, after loading of CyDye-labeled ligand, receptor and testing compounds to the multi-unit plate, the PL value in each reaction unit of the plate measured by using a fluorescence polarization reader reflects the binding capacity of the testing compound to the receptor.

It is also an ideal device for synthesis of tiny amount of peptides or oligo-nucleotides with solid-phase synthesis approach, because the synthesis contains multiple loading, emptying and washing steps. By defining the loading sequence of desired reagents through the conjunction with reservoir plates, one can easily control the length and sequence of peptide or oligo-nucleotide in each addressed reaction unit. Alternatively, tiny beads may be introduced into the reaction chamber to provide more surface area for the synthesis.

Because of easy liquid handling, the device can be used for a solid phase enzymatic assay for compound screening in order to eliminate interference of colored compounds on the results, which is frequently encountered. The procedures of the solid phase enzymatic assay are 1) to immobilize the enzyme to the surface of the reaction chambers through physical interaction or chemical reaction, 2) to wash away un-bound enzyme, 3) to introduce compounds into the reaction chambers and to form enzyme-compound complexes, 4) to wash away free compounds, 5) to load substrate into reaction chambers for reaction and 6) to analyze the enzyme activity by use of a device such as micro-well reader. When a compound is able to bind to enzyme and inhibit the enzyme, the enzyme activity will decrease.

The device can also be used for compound screening using a mass spectroscopy approach. The procedure are 1) to immobilize target protein to the surface of the reaction chambers through physical interaction or chemical reaction, 2) to wash away un-bound protein, 3) to introduce compounds into the reaction chambers and to form protein-compound complexes, 4) to wash away free compounds, 5) to free the compound from protein-compound complexes through chemical or physical treatment, 6) to analyze the freed compound by mass spectroscopic methods.

The top loading feature of the device can also be used for automation to simplify the procedure such as washing step in which same solution need to be transferred in and out of the device several times. Instead of bottom touch loading, a liquid handling device for example a multi-channel tubing pump can continuously introduce washing buffer into the non-capillarity zone to wash away unbound analytes or compounds from the device by several volume of washing buffer flowing through the capillarity reaction chamber.

The present invention has been described using detailed descriptions of embodiments thereof that are provided by way of example and are not intended to limit the scope of the invention. The described embodiments comprise different features, not all of which are required in all embodiments of the invention. Some embodiments of the present invention utilize only some of the features or possible combinations of the features. Variations of embodiments of the present invention that are described and embodiments of the present invention comprising different combinations of features noted in the described embodiments will occur to persons of the art. The usefulness should not be limited by these examples and embodiments but should include the following claims as well.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

The invention claimed is:

1. A reaction unit comprising:
a tubular first chamber having:
a first interior space which is a capillary and has a first cross-section having a first diameter,
wherein the first interior space is configured so that a liquid fills the interior space fully with a fully quantitative amount of said liquid by capillary force; and
a second chamber having:
a second interior space of cylindrical shape whose second cross-section has a second diameter which is larger than the first diameter and is non-capillary,
wherein the first chamber and the second chamber are coupled or integrally formed to create the reaction unit via a third area having an interior space, wherein the first interior space of the first chamber is separated from the interior space of the third area by a well-defined edge,
wherein the interior space of the third area has a conical shape or dome shape widening from the first interior space to the second interior space, is a non-capillary area and limits the liquid in the first chamber to said fully quantitative amount, and
wherein the reaction unit is configured to receive liquid at the first chamber and carry the liquid toward the second chamber against gravity.

2. The reaction unit according to claim 1, wherein the first chamber and the second chamber are arranged coaxially to each other or at an angle to each other.

3. The reaction unit according to claim 1, wherein the first interior space of the first chamber has a shape of a cylinder, cone or parabola, square, is rectangular, triangular, circular, oval, has a star-like cross-section or a combination thereof.

4. The reaction unit according to claim 1, wherein the reaction unit has an open top structure for allowing air to pass through while liquid transfers into or from the first chamber.

5. The reaction unit according to claim 1, wherein the reaction unit has an open bottom structure through which liquid can flow into or out of the first chamber under said capillary action.

6. The reaction unit according to claim 4, wherein the reaction unit has an open bottom structure through which liquid can flow into or out of the first chamber under the capillary action.

7. The reaction unit according to claim 1, wherein the diameter of the first cross-section is 0.01 mm to 3 mm.

8. The reaction unit according to claim 1, wherein the third area is dome shaped.

9. A multi-unit plate comprising a plurality of reaction units being incorporated into or attached to a plate body, wherein each of the reaction units is a reaction unit according to claim 1.

10. The multi-unit plate according to claim 9, wherein the first chambers have different sizes suitable to take up different volumes of liquid.

11. The reaction unit according to claim 1, wherein the first chamber is an open capillary chamber having a lateral gap.

12. The reaction unit of claim 1, wherein the reaction unit is integrally formed.

13. The reaction unit of claim 3, wherein the shape is that of a cylinder.

* * * * *